United States Patent
Shelly (10) Patent No.: US 11,837,106 B2
(45) Date of Patent: Dec. 5, 2023

(54) SYSTEM AND METHOD TO MONITOR AND TITRATE TREATMENT FOR HIGH ALTITUDE-INDUCED CENTRAL SLEEP APNEA (CSA)

(71) Applicant: KONINKLIJKE PHILIPS N.V., Eindhoven (NL)

(72) Inventor: Benjamin Irwin Shelly, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 430 days.

(21) Appl. No.: 17/106,827

(22) Filed: Nov. 30, 2020

(65) Prior Publication Data

US 2022/0020501 A1    Jan. 20, 2022

Related U.S. Application Data

(60) Provisional application No. 63/054,197, filed on Jul. 20, 2020.

(51) Int. Cl.
*G09B 19/00* (2006.01)
*G16H 20/60* (2018.01)
(Continued)

(52) U.S. Cl.
CPC ............ *G09B 19/00* (2013.01); *A61B 5/0205* (2013.01); *A61B 5/0531* (2013.01);
(Continued)

(58) Field of Classification Search
CPC ..... G09B 19/00; A61B 5/0205; A61B 5/0531; A61B 5/0806; A61B 5/14551;
(Continued)

(56) References Cited

U.S. PATENT DOCUMENTS

| | | | |
|---|---|---|---|
| 2005/0061319 A1* | 3/2005 | Hartley | A61B 5/4812 128/204.23 |
| 2005/0061320 A1* | 3/2005 | Lee | A61N 1/36514 128/204.23 |

(Continued)

FOREIGN PATENT DOCUMENTS

| | | |
|---|---|---|
| CA | 2968645 A1 | 7/2016 |
| WO | 2020047603 A1 | 3/2020 |

(Continued)

OTHER PUBLICATIONS

Hanley, Marisol A. "A predictive model of health-related quality of life in obstructive sleep apnea." ProQuest Dissertations and Theses. ProQuest Dissertations Publishing. (2002) (Year: 2002).*

(Continued)

*Primary Examiner* — Linh Giang Le (57) ABSTRACT

An apparatus and method for employing data from the person and from the environment where the person is situated facilitate the detection and prediction of severity of high altitude-induced Sleep Disordered Breathing (SDB, and specifically Central Sleep Apnea (CSA)). Longitudinal tracking of local barometric pressure and severity of SDB symptoms (objective or subjective or both) allow for prediction of occurrence of SDB (per altitude). Some of all of the data can be obtained from one or more wearable devices that may be worn by the person. Additionally, personalized mapping for dosing of medication (e.g. acetazolamide, low-flow oxygen therapy) to treat high altitude-induced SDB are provided, with recommended dosing provided to the person per altitude.

12 Claims, 4 Drawing Sheets

(51) Int. Cl.

| | |
|---|---|
| *A61B 5/0205* | (2006.01) |
| *A61B 5/0531* | (2021.01) |
| *A61B 5/16* | (2006.01) |
| *A61B 5/00* | (2006.01) |
| *A61K 31/4045* | (2006.01) |
| *G16H 50/50* | (2018.01) |
| *A61B 5/08* | (2006.01) |
| *A61B 5/1455* | (2006.01) |
| *A61M 16/00* | (2006.01) |
| *G16H 40/67* | (2018.01) |
| *G16H 10/60* | (2018.01) |
| *G16H 50/30* | (2018.01) |
| *G16H 50/70* | (2018.01) |
| *G16H 50/20* | (2018.01) |
| *G06N 3/08* | (2023.01) |
| *G16H 20/10* | (2018.01) |
| *G16H 10/20* | (2018.01) |
| *G16H 20/00* | (2018.01) |
| *G06N 20/00* | (2019.01) |
| *G16H 20/30* | (2018.01) |
| *G06N 5/02* | (2023.01) |
| *A61B 5/024* | (2006.01) |
| *A61B 5/11* | (2006.01) |

(52) U.S. Cl.
CPC ........ *A61B 5/0806* (2013.01); *A61B 5/14551* (2013.01); *A61B 5/165* (2013.01); *A61B 5/486* (2013.01); *A61B 5/4815* (2013.01); *A61B 5/4818* (2013.01); *A61B 5/4836* (2013.01); *A61B 5/4839* (2013.01); *A61B 5/4842* (2013.01); *A61B 5/4848* (2013.01); *A61B 5/7267* (2013.01); *A61B 5/7275* (2013.01); *A61B 5/7475* (2013.01); *A61K 31/4045* (2013.01); *A61M 16/0003* (2014.02); *A61M 16/024* (2017.08); *A61M 16/026* (2017.08); *G06N 3/08* (2013.01); *G06N 5/02* (2013.01); *G06N 20/00* (2019.01); *G16H 10/20* (2018.01); *G16H 10/60* (2018.01); *G16H 20/00* (2018.01); *G16H 20/10* (2018.01); *G16H 20/30* (2018.01); *G16H 20/60* (2018.01); *G16H 40/67* (2018.01); *G16H 50/20* (2018.01); *G16H 50/30* (2018.01); *G16H 50/50* (2018.01); *G16H 50/70* (2018.01); *A61B 5/02405* (2013.01); *A61B 5/1118* (2013.01); *A61B 5/4806* (2013.01); *A61B 2560/0242* (2013.01); *A61B 2560/0257* (2013.01); *A61B 2562/0219* (2013.01); *A61M 2205/3303* (2013.01); *A61M 2205/3584* (2013.01); *A61M 2205/502* (2013.01)

(58) Field of Classification Search
CPC ..... A61B 5/165; A61B 5/4815; A61B 5/4818; A61B 5/4836; A61B 5/4839; A61B 5/4842; A61B 5/4848; A61B 5/486; A61B 5/7267; A61B 5/7275; A61B 5/7475; A61B 5/02405; A61B 5/1118; A61B 5/4806; A61B 2560/0242; A61B 2560/0257; A61B 2562/0219; A61K 31/4045; A61M 16/0003; A61M 16/024; A61M 16/026; A61M 2205/3303; A61M 2205/3584; A61M 2205/502; G06N 3/08; G06N 5/02; G06N 20/00; G16H 10/20; G16H 10/60; G16H 20/00; G16H 20/10; G16H 20/30; G16H 20/60; G16H 40/67; G16H 50/20; G16H 50/30; G16H 50/50; G16H 50/70; G16H 20/40; G16H 20/70; G16H 40/63

See application file for complete search history.

(56) References Cited

U.S. PATENT DOCUMENTS

| | | |
|---|---|---|
| 2009/0177702 A1 | 7/2009 | Stahmann |
| 2010/0174335 A1 | 7/2010 | Stahmann |

FOREIGN PATENT DOCUMENTS

| | | | |
|---|---|---|---|
| WO | 2020142858 A1 | 7/2020 | |
| WO | WO-2021091902 A1 * | 5/2021 | ........... A61K 31/138 |

OTHER PUBLICATIONS

Ginosar, Yehuda et al, "High Altitude, Continuous Positive Airway Pressure, and Obstructive Sleep Apnea; Subjective Observations and Objective Data", High Altitude Medicine & Biology, vol. 14, No. 2, 2013.

* cited by examiner

SYSTEM AND METHOD TO MONITOR AND TITRATE TREATMENT FOR HIGH ALTITUDE-INDUCED CENTRAL SLEEP APNEA (CSA)

CROSS-REFERENCE TO PRIOR APPLICATIONS

This application claims the benefit of U.S. Provisional Application No. 63/054,197, filed on 20 Jul. 2020. This application is hereby incorporated by reference herein.

BACKGROUND OF THE INVENTION

1. Field of the Invention

The present invention pertains to Central Sleep Apnea (CSA), and, in particular, to an apparatus and method for monitoring and titration treatment for high altitude-induced CSA.

2. Description of the Related Art

High altitude-induced central sleep apnea is a common disorder, with as much as 25% of the population exhibiting symptoms at 7500 feet of elevation and approximately 85% of the population exhibiting symptoms above 12,000 feet of elevation. At high altitudes, respiratory alkalosis is common and can lead to ventilatory instability, particularly due to the lowering of the difference between PaCO2 and the apneic threshold, but may also be due to hypocapnic increase in loop gain. During sleep, this ventilatory instability manifests as periodic pauses in breathing exceeding ten seconds in duration, typically associated with blood oxygen desaturations, sleep fragmentation, and other sequelae, like headache, fatigue, difficulty maintaining sleep (sleep maintenance insomnia), etc. The pauses in breathing are most typically due to the cessation of respiratory effort (central apneas), but obstructive sleep apnea may also significantly worsen at altitude due to a change in loop gain.

High altitude-induced central sleep apnea is commonly treated by acetazolamide (Diamox), often prophylactically, and/or by nocturnal supplemental low flow oxygen. Both treatments have problematic side effects, including paresthesia, headache, nausea, frequent urination, and altered sense of taste for acetazolamide. Low flow oxygen usage has side effects of skin irritation and nasal dryness. Low flow oxygen therapy may not be preferred for treatment in many cases due to the inconvenience of using and transporting low flow oxygen therapy (i.e. nasal cannula and oxygen concentrator or compressed oxygen cylinders).

As such, improvements in the way in which high altitude-induced central sleep apnea is monitored and treated would be desirable.

SUMMARY OF THE INVENTION

Accordingly, it is an object of the present invention to provide an improved apparatus and method for monitoring and providing titration treatment for high altitude-induced central sleep apnea that overcomes the shortcomings of conventional systems and methods for providing monitoring and treatment of a person who suffers from high altitude-induced central sleep apnea. This object is achieved according to one embodiment of the present invention by providing an apparatus and method wherein data from the person and from the environment where the person is situated facilitate the detection and prediction of severity of high altitude-induced sleep disordered breathing (SDB, and specifically central sleep apnea). Longitudinal tracking of local barometric pressure and severity of SDB symptoms (objective or subjective or both) allow for prediction of occurrence of SDB (per altitude). Some of all of the data can be obtained from one or more wearable devices that may be worn by the person. Additionally, personalized mapping for dosing of medication (e.g. acetazolamide, low-flow oxygen therapy) to treat high altitude-induced SDB are provided, with recommended dosing provided to the person per altitude.

High altitude-induced central sleep apnea cannot be diagnosed in the field currently, nor have treatment dynamically titrated. In accordance with the disclosed and claimed concept, however, a wearable device comprising barometric pressure sensor, photoplethysmograph, accelerometer, and gyroscope monitor effective altitude and severity of sleep disordered breathing longitudinally for a person. If sleep disordered breathing is noted (or severity is significantly increased) at higher altitude but not a lower altitude, the person is diagnosed with high altitude-induced sleep disordered breathing.

If a person has been diagnosed with high altitude-induced sleep disordered breathing, then system tracks altitude, SDB severity, and treatment dosing in order to determine optimal treatment dosing strategy for the given altitude and predicts appropriate dosing for subsequent nights based on altitude.

Accordingly, aspects of the disclosed and claimed concept are provided by an improved method of modeling altitude-induced Central Sleep Apnea (CSA) in a person, the general nature of which can be stated as including determining a number of Sleep-Disordered Breathing (SDB) severity values and a number effective altitude values for each of a number of periods of sleep of the person, each SDB severity value of the number of SDB severity values corresponding with an effective altitude value of the number effective altitude values, based at least in part upon at least a subset of the number of SDB severity values and at least a subset of the number of effective altitude values, determining an effective altitude at which the person is likely to suffer from a predetermined level of SDB severity, and generating an output that is based at least in part upon the effective altitude.

Other aspects of the disclosed and claimed concept are provided by an improved method of determining dosage of an altitude-induced Central Sleep Apnea (CSA) treatment for a person, the general nature of which can be stated as including, for each of a number of periods of sleep of the person, determining a number of Sleep-Disordered Breathing (SDB) severity values, each SDB severity value of the number of SDB severity values being based at least in part upon a corresponding effective altitude value and a corresponding dosage of a CSA treatment, for a given effective altitude, determining based at least in part upon at least a subset of the number of Sleep-Disordered Breathing (SDB) severity values, a preferred dosage of the CSA treatment at which a likely SDB severity value is no greater than a predetermined SDB severity value, and generating an output that is based at least in part upon the dosage.

Other aspects of the disclosed and claimed concept are provided by an improved apparatus structured to determine dosage of an altitude-induced Central Sleep Apnea (CSA) treatment for a person, the general nature of which can be stated as including a processor apparatus that can be generally stated as including a processor and a storage, an input apparatus structured to provide a number of input signals to the processor apparatus, an output apparatus structured to receive a number of output signals from the processor apparatus, and the storage having stored therein a number of instructions which, when executed on the processor, cause the apparatus to perform a number of operations, the general nature of which can be stated as including, for each of a number of periods of sleep of the person, determining a number of Sleep-Disordered Breathing (SDB) severity values, each SDB severity value of the number of SDB severity values being based at least in part upon a corresponding effective altitude value and a corresponding dosage of a CSA treatment, for a given effective altitude, determining based at least in part upon at least a subset of the number of Sleep-Disordered Breathing (SDB) severity values, a preferred dosage of the CSA treatment at which a likely SDB severity value is no greater than a predetermined SDB severity value, and generating an output that is based at least in part upon the dosage.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various FIG.s. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
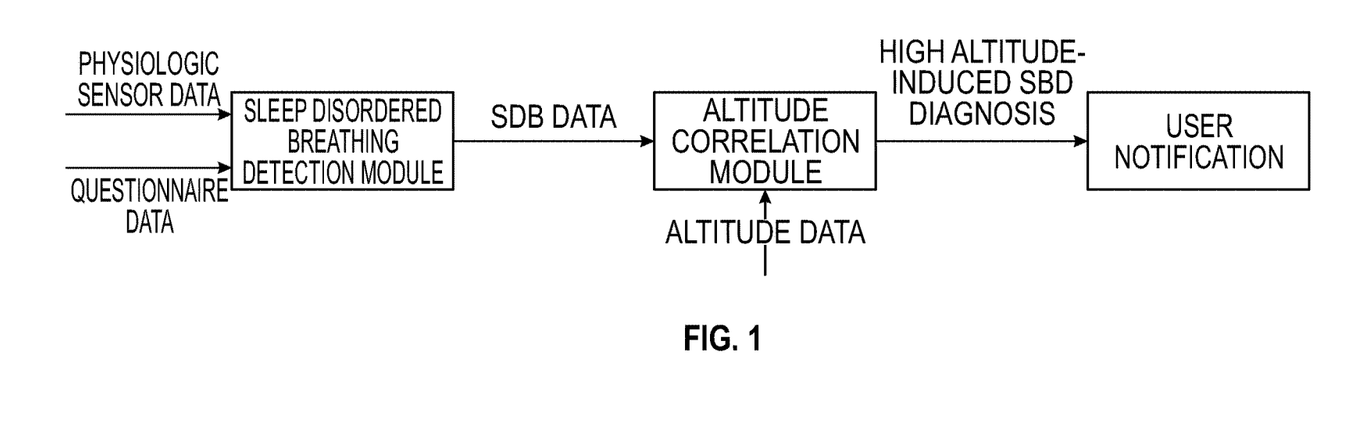
FIG. 1 is a block diagram for system to diagnose high-altitude induced sleep disordered breathing in accordance with an aspect of the disclosed and claimed concept.
Figure 2:
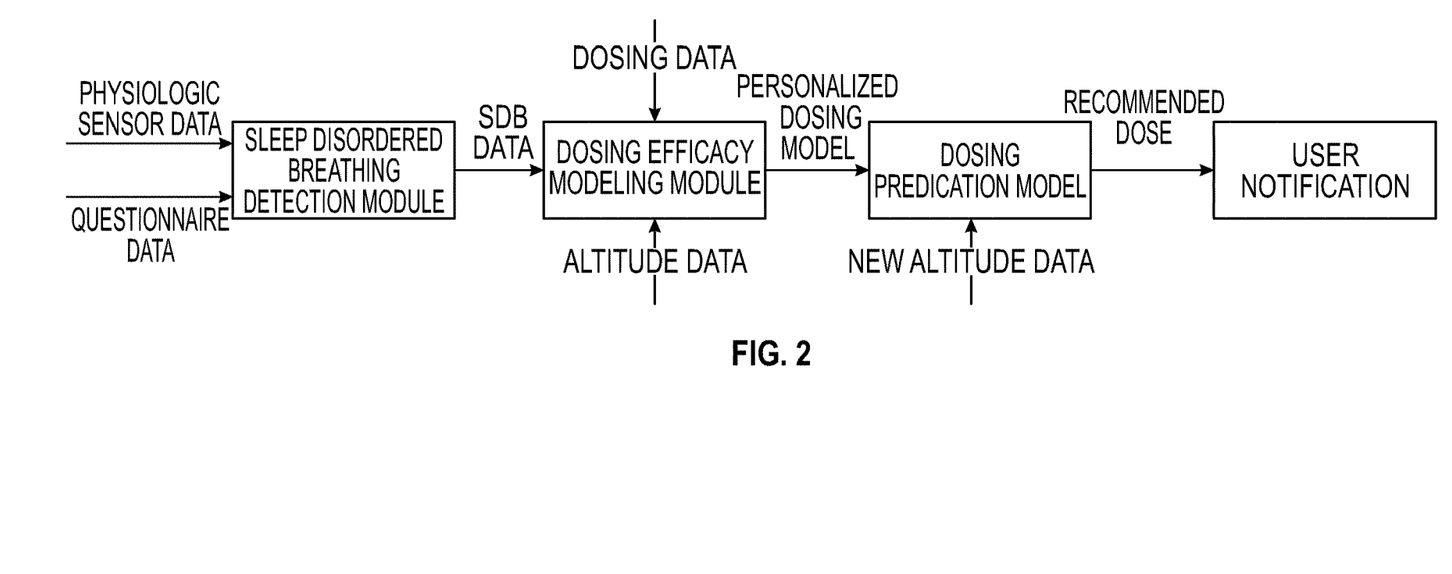
FIG. 2 is a block diagram for system to automatically recommend dosing of therapy for high altitude-induced sleep disordered breathing in accordance with an aspect of the disclosed and claimed concept.

The disclosed and claimed concept shown in FIGS. 1 and 2 includes several different modules, such as a sleep disordered breathing (SDB) detection module, an altitude correlation module, a therapy dosing/efficacy modeling module, and a dosing prediction module.

System Architecture

In an embodiment where the system provides diagnosis only, the block diagram showing the components of the system is depicted generally in FIG. 1. In another embodiment where the system provides automatic titration of therapy for altitude-induced sleep disordered breathing, see the block diagram in FIG. 2.

Sleep Disordered Breathing Detection Module

The intent of the sleep disordered breathing detection module is to determine the presence and severity of sleep disordered breathing, preferably on a nightly basis. As known to one skilled in the art, a number of different methodologies exist to assess sleep disordered breathing severity. As employed herein, the expression "a number of" and variations thereof shall refer broadly to any non-zero quantity, including a quantity of one.

Physiologic Sensor Data

In the disclosed and claimed concept, physiological sensor data can be obtained from a photoplethysmograph (PPG) with appropriate electromagnetic spectral components to monitor both pulsatile blood volume changes as well as SpO2, and an accelerometer/gyroscope to measure actigraphy in a wearable form factor such as a smart watch or other wearable device. In some embodiments, only a subset of the signals mentioned are measured. Alternative embodiments may use different sensor configurations, such as with the use of microphones, optical sensor, piezoelectric sensors, etc.

Questionnaire Data

In the disclosed and claimed concept, sleep quality questionnaire data is gathered from the person. Exemplary questions include, "How refreshing would you rate your night of sleep?" and "How long did it take you to fall asleep?" Other questions that similarly assess sleep quality or the impact of sleep quality could also be used. In other embodiments, subjective user data is not required. An example of the scaling for "How refreshing would you rate your night of sleep?" could be a series of boxes numbered 0 for "terrible" though 10 for "excellent".

SDB Data Output

In the disclosed and claimed concept, the SDB data is a digital severity scale that comprises a function of an objective measure of SDB severity (Obj. SDB Measure) and a subjective measure of sleep quality (Subj. SDB Measure). In an exemplary embodiment, the objective and subjective measures are combined according to the following Equation 1:

$$\text{SDB Severity} = \min(((\min(\text{Obj. SDB Measure}, 50)/5) + (10 - \text{Subj. SDB Measure})/5), 10)$$

In this embodiment, a purpose of the combining Equation 1 is to allow for both Objective and Subjective SDB measures to influence the SDB severity weighting and provide a scaled output on a ten point scale. This allows for persons who have a high degree of subjective dissatisfaction with their sleep caused my lower amounts of objective SDB to still be appropriately treated. For instance, in this embodiment, a high level of SDB Severity, i.e. a level of "10" denotes greater severity, (e.g. an AHI>=50 or an AHI of 40 with a "terrible" night of sleep) and a low level of SDB severity is preferable. Other functions for combining the Subjective and Objective SDB Measures are also considered. It is reiterated, however, that the disclosed and claimed concept contemplates the use of effective altitude in combination with only objective or only subjective data.

Objective SDB Measure

In the disclosed and claimed concept, the PPG/SpO2 and Actigraphy signals are processed to determine a Central Apnea Index (CAI), i.e., the number of central apneas per hour of sleep. In another disclosed and claimed concept, a full Apnea/Hypopnea Index (AHI) is used. In order to determine the CAI or AHI, the system processes the PPG and accelerometer sensors to determine indications of arousals, respiratory cessations, and oxygen desaturations. In other embodiments, only the SpO2 signal is used in order to determine an Oxygen Desaturation Index (ODI) for the objective SDB measure. Other measures that can be used for objective sleep disordered breathing severity include indices of arousal (e.g. arousal index, which is the number of heart rate accelerations, etc.), sleep fragmentation (e.g. number of awakenings), Wakeup After Sleep Onset (WASO, which is usually measured as the total number of minutes awake after initially falling asleep), etc.

Subjective SDB Measure

In the disclosed and claimed concept, the subjective SDB measure is the answer to a single question, such as: "On a scale of zero to ten, how refreshing would you rate your sleep last night?". In other embodiments, a number of questions are asked and a subjective SDB measure is a scored aggregate response to the number of questions. Questions asked to determine the subjective SDB measure can be related to daytime function such as alertness, fatigue, etc., and/or sleep quality/satisfaction, and questions may be asked once or multiple times throughout the day.

Altitude Correlation Module

A purpose of the Altitude correlation module is to determine an altitude at which a person is likely to suffer a predetermined level of SDB, which typically would be a significant level of SDB. The altitude correlation module also advantageously determines a function which can be extrapolated and interpolated in order to determine a predicted degree of SDB severity at different altitudes. The altitude correlation module takes as inputs the SDB severity and a measure of altitude at which the SDB severity was determined. The altitude correlation module determines an altitude at which the severity of SDB exceeds (or is projected to exceed) a predetermined level of severity. In the disclosed and claimed concept, the predetermined level is two out of the ten point scale, which would be an increase in AHI of approximately 10, depending on daytime impact.

Figure 3:
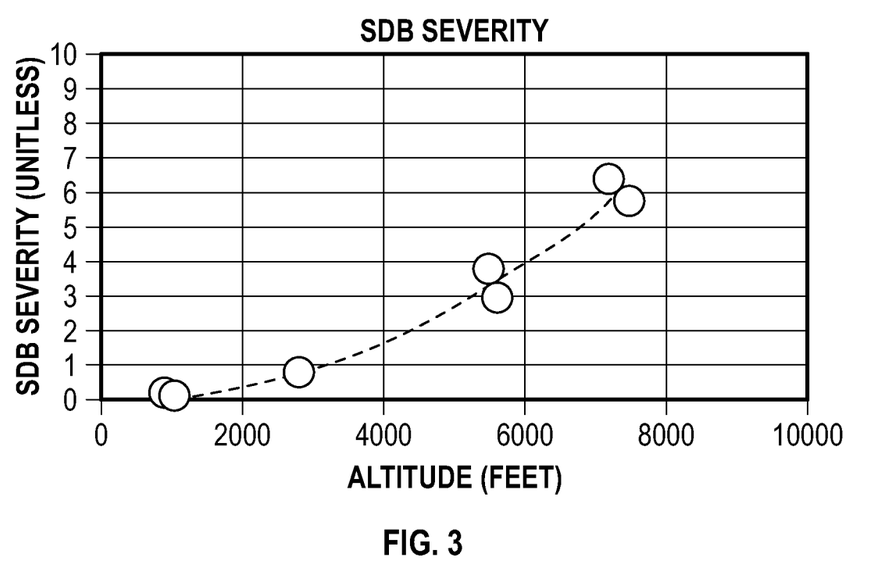
FIG. 3 is an example plot of daily SDB Severity vs. Altitude with curve fit, in which a person experiences significant high altitude induced SDB at above 4000 feet effective elevation.

An example shown in FIG. 3 depicts daily SDB severity ratings and corresponding altitudes for a person traveling to different altitudes. The person in the example below has significant altitude-induced sleep disordered breathing at any altitude above 4000 feet.

Figure 4:
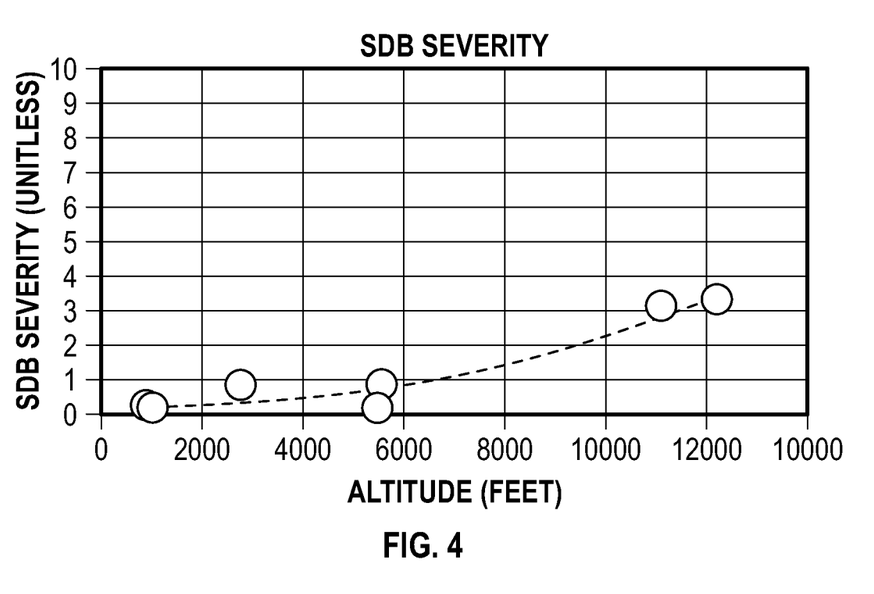
FIG. 4 is an example plot of daily SDB Severity vs. Altitude with curve fit, in which a person is less sensitive to altitude and experiences significant high altitude induced SDB at above 9500 feet effective elevation.

An example shown in FIG. 4 depicts daily SDB severity ratings and altitudes for another person traveling to different altitudes. The person in the FIG. 4 example has is less sensitive to altitude and only shows signs of altitude-induced sleep disordered breathing above 9500 feet.

Figure 5:
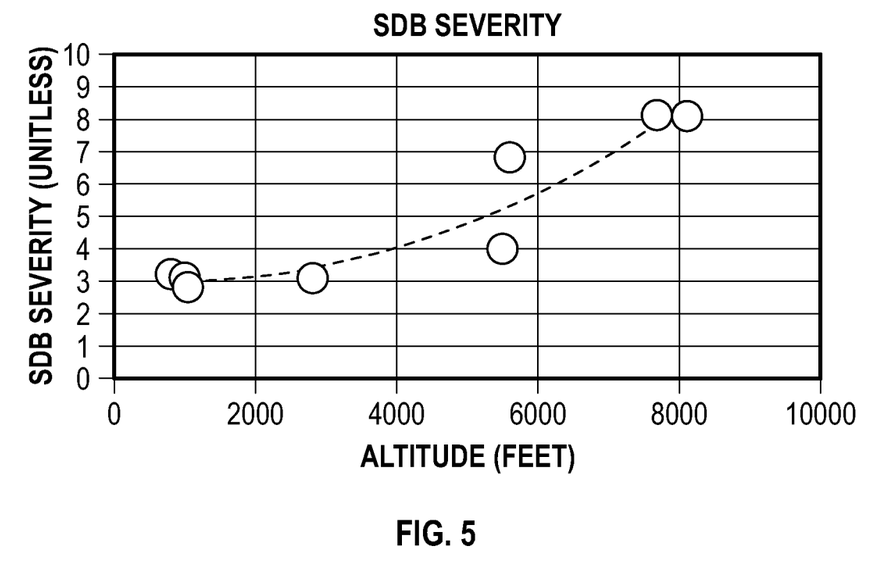
FIG. 5 is an example plot of daily SDB Severity vs. Altitude with curve fit, in which a person experiences significant SDB at any altitude and has a significant elevation of SDB (altitude-induced sleep disordered breathing) above 5000 feet effective elevation.

Another example shown in FIG. 5 depicts daily SDB severity ratings and altitudes for yet another person traveling to different altitudes. The person in the FIG. 5 example has significant SDB at any altitude and has a significant elevation of SDB (altitude-induced sleep disordered breathing) above 5000 feet, noted due to the increase in projected SDB severity by at least two units.

In the disclosed and claimed concept, the SDB correlation module derives an exemplary quadrative curve fit for the SDB severity according to the altitude using a least squares error methodology. Other curve form factors such as exponential, power, etc., and curve fitting methodologies are also within the scope of the disclosed and claimed concept, including piecewise linear and nonlinear, etc.

Altitude Data

In the disclosed and claimed concept, the altitude data is provided by a barometric pressure sensor on the wearable device to estimate the current effective altitude for the night that the SDB Severity Metric is determined. In this embodiment, barometric pressure is measured in kPa and correlated to effective altitude (e.g. sea level=101 kPa, 5000 feet altitude=84.3 kPa, 10,000 feet altitude=69.7 kPa, etc.). In other embodiments, barometric pressure or altitude is provided by other means, including GPS, direct user data entry, communication with another device such as a smartphone, etc.

High Altitude-Induced SDB Diagnosis and User Notification

In the disclosed and claimed concept, the person is notified any time they are at an altitude greater than the altitude at which they are predicted to have significant altitude-induced SDB according to the Altitude correlation module that determines that the person is at elevated risk for SDB. Examples of notification include smartphone or smartwatch notification, email, etc. In some embodiments, notification is only made when the person is approaching a habitual bedtime. In other embodiments, the person is presented a report of data prepared by the correlation module to present to a physician, and the report may look like the plots shown in FIGS. 3-5, by way of example, in order to facilitate a prescription for therapy, such as acetazolamide.

Dosing Efficacy Modeling Module

In the embodiment where therapy dosing is also provided, the Dosing efficacy modeling module takes as input the SDB severity, the current effective altitude, and the current dosing. An intent of this module is to determine a function from which appropriate dosing of therapy can be determined. Ideally, a minimum dosage that is required to achieve efficacy is suggested, so that side effects can be mitigated (for pharmacological therapy) or so that oxygen can be conserved (for low flow oxygen therapy).

Dosing Data

In the disclosed and claimed concept, daily dosing is provided manually by the person, i.e., dosage of Diamox of 125 mg or 2 LPM of low flow oxygen. In other embodiments, dosing information is provided automatically, such as by an oxygen delivery device or a medication dispenser.

Personalized Dosing Model

In the disclosed and claimed concept, the dosing model that is used to derive projected SDB at a given altitude and dosage is as follows in Equation 2, which employs a minimum SDB severity "C" that is equal to the SDB severity in the person at sea level. Equation 2 also takes into consideration effective altitude (Altitude) and dosage of SDB therapy (Dose).

$$\text{SDB Severity} = \max((A*\text{Altitude}^2 + B*\text{Altitude} - D*\text{Dose}), 0) + C$$

In Equation 2, the coefficients A and B are curve fit coefficients derived by curve fitting software or are derived in other fashions. Other forms of this equation are also contemplated, including nonlinear functions.

In the disclosed and claimed concept, the personalized dosing model has pre-defined data from other persons with similar altitude sensitivity (altitudes at which SDB>threshold) in order to provide an initial model. Such an initial data set is used prior to the development of data for the person obtained from SDB severity of the person that is based upon corresponding effective altitude and dosage values and SDB severity at sea level for the person. In this embodiment, the model for the person is continuously updated with new data and generated by Kalman filtering. In another embodiment, the model is generated using a least squares error estimate.

Dosing Prediction Module

A purpose of the dosing prediction module is to provide the person with a recommended dosage in order to ameliorate high altitude-induced SDB for a given effective altitude. In the disclosed and claimed concept, the Personalized Dosing Module and the current effective altitude are used to determine a dose at which the SDB severity would be no greater than SDB Severity at sea level plus one. In other embodiments, other thresholds for dosing are also possible.

Dosing User Notification

In the disclosed and claimed concept, the person is notified any time they are at an altitude greater than the altitude at which they are predicted to have significant altitude-induced SDB according to the Altitude correlation module. Such notification may indicate that the person is at an elevated risk for SDB, meaning SDB severity above a predetermined threshold or value, and may further indicate an appropriate dosing of therapy that would be desirable in order to ameliorate symptoms. Examples of notification include smartphone or smartwatch notification, email, etc. In some embodiments, notification is only made when the person is approaching a habitual bedtime. In other embodiments, the notification is made at times when the person is indicated (e.g. by self-report or otherwise) to take medication. In other embodiments, the person is presented a report of data prepared by the Dosing Prediction module to present to a physician in order to facilitate a prescription for therapy or ranges of dosing of therapy (e.g. acetazolamide).

Apparatus and Method

Figure 6:
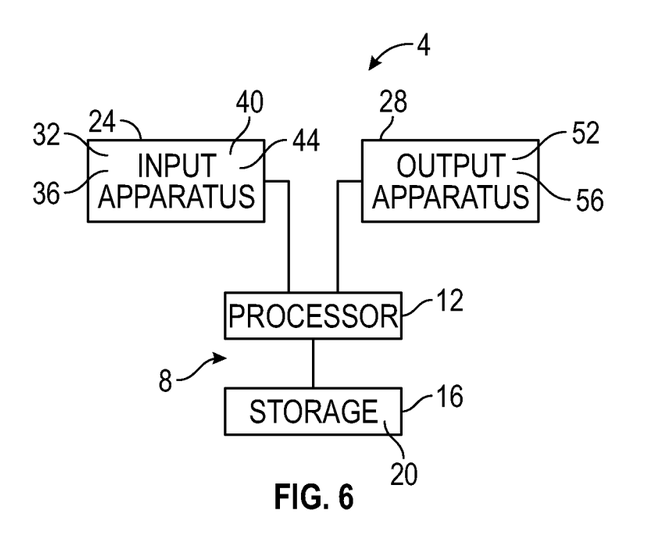
FIG. 6 depicts an apparatus in accordance with the disclosed and claimed concept.

An improved apparatus 4 in accordance with the disclosed and claimed concept is depicted in a schematic fashion in FIG. 6. Apparatus 4 can be employed in performing an improved method 100 and an improved method 200 that are likewise in accordance with the disclosed and claimed concept and at least a portion of which are depicted in a schematic fashion in FIGS. 7 and 8. Apparatus 4 can be characterized as including a processor apparatus 8 that can be said to include a processor 12 and a storage 16 that are connected with one another. Storage 16 is in the form of a non-transitory storage medium has stored therein a number of routines 20 that are likewise in the form of a non-transitory storage medium and that include instructions which, when executed on processor 12, cause apparatus 4 to perform certain operations such as are mentioned elsewhere herein. As noted elsewhere herein, apparatus 4 can be in any of variety of forms and can be in the form of a wearable device such as a smart watch or the like and can likewise be in the form of a cellular telephone or the like.

Apparatus 4 can be said to further include an input apparatus 24 that provides input signals to processor 12 and an output apparatus 28 that receives output signals from processor 12. Input apparatus 24 can be said to include any of a variety of input components, and output apparatus 28 can likewise be said to include any of a variety of output components. For instance, if apparatus 4 includes a touchscreen, output apparatus 28 might be said to include a visual display of the touchscreen, and input apparatus 24 might be said to include a touch-sensitive overlay that is situated atop the visual display.

Input apparatus 24 can be said to include a wide variety of monitoring devices such as, by way of example and without limitation, a PPG monitoring device 32, an atmospheric pressure monitoring device 36, a GPS monitoring device 40, an accelerometer/gyroscope 44, and any of a variety of other monitoring devices such as microphones, optical sensors, piezoelectric sensors, etc., each of which input signals that are input by input apparatus 24 as input signals to processor 12.

Output apparatus 28 includes a number of output devices that include a visual display 52 and a control actuator 56. Visual display 52 can visually depict the subject matter of, for instance, FIGS. 3-5 and/or can depict an instruction to a clinician in the form of a prescription.

Control actuator 56 is usable in any of a wide variety of fashions, such as to provide to individualized sleep therapy. In this regard, it can be understood that control actuator 56 and input apparatus 24, in conjunction with processor apparatus 8 and the routines 20, can form a closed-loop control system that adapts a customized prescription dosage to the person or an oxygen flow rate to the person. Other methods of execution of routines 20 may include machine learning modules, etc., in order to improve personalized accuracy for the user at the expense of simplicity of implementation.

Figure 7:
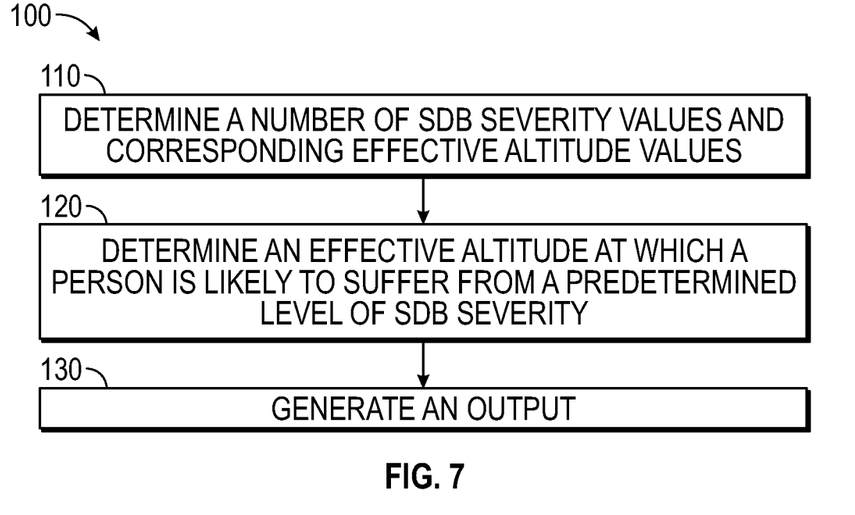
FIG. 7 depicts an improved method in accordance with the disclosed and claimed concept.

An improved method 100 in accordance with the disclosed and claimed concept is depicted generally in FIG. 7. Processing begins, as at 110 with the determining of the number of SDB severity values and corresponding effective altitude values. In this regard, it is understood that and effective altitude value typically is in the form of an atmospheric pressure that may currently exist and that may be where the person is situated.

Processing continues, as at 120, with the determining of an effective altitude at which a person is likely to suffer from a predetermined level of SDB severity. The predetermined level of SDB severity can be such as is described elsewhere herein or can be otherwise established. Processing continues, as at 130, with the generating of an output which can be, for instance, a plot such as is depicted generally in FIGS. 3-5.

Figure 8:
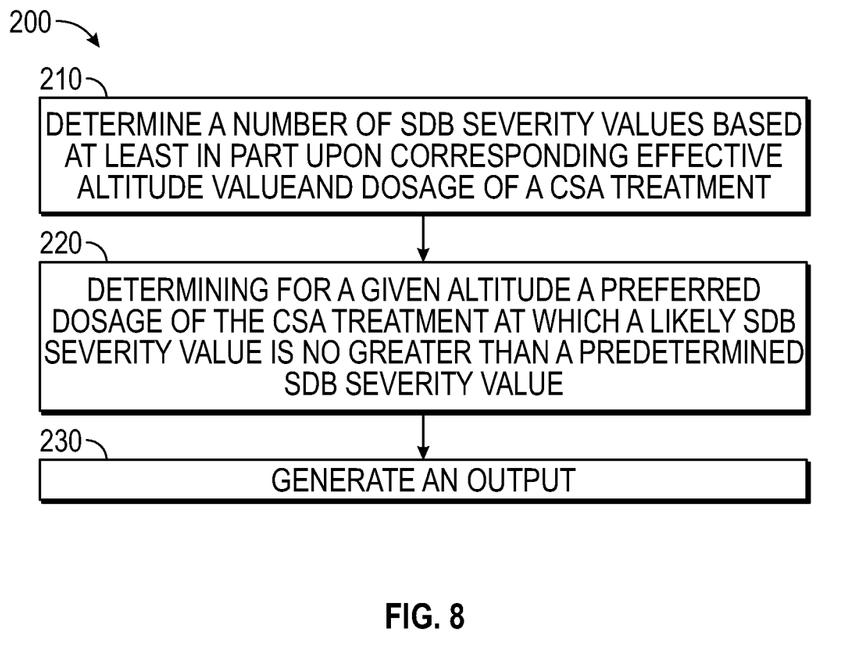
FIG. 8 depicts another improved method in accordance with the disclosed and claimed concept.

Another improved method 200 in accordance with the disclosed and claimed concept is depicted generally in FIG. 8. Processing begins, as at 210 with the determining of a number of SDB severity values, each being based at least in part upon a corresponding effective altitude value and a dosage of CSA treatment. Processing continues, as at 220, with the determining, for a given altitude, of a preferred dosage of the CSA treatment at which a likely SDB severity value is no greater than a predetermined SDB severity value. Processing continues, as at 230, with the generating of an output.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of automatically and dynamically titrating treatment for altitude-induced Central Sleep Apnea (CSA) for a person using a wearable device structured to be worn on a body of the person and having a processor apparatus, comprising:
   for each of a number of periods of sleep of the person, determining in the wearable device a number of Sleep-Disordered Breathing (SDB) severity values, each SDB severity value of the number of SDB severity values being based at least in part upon a corresponding effective altitude value and a corresponding dosage of a CSA treatment;
   automatically determining in the wearable device a current effective altitude of the person;
   determining in the wearable device based at least in part upon at least a subset of the number of Sleep-Disordered Breathing (SDB) severity values and the current effective altitude, a preferred dosage of the CSA treatment at which a likely SDB severity value is no greater than a predetermined SDB severity value; and
   generating an output from the wearable device indicating a recommended treatment for CSA at the preferred dosage of the CSA treatment.

2. The method of claim 1 wherein the preferred dosage is a minimum dosage of the CSA treatment at which the likely SDB severity value is no greater than the predetermined SDB severity value.

3. The method of claim 1, further comprising generating the output at a time approaching a habitual bedtime of the person.

4. The method of claim 1 wherein the output is further representative of the person being at or above the current effective altitude.

5. The method of claim 1 wherein each SDB severity value of at least some of the number of SDB severity values is further based at least in part upon an SDB severity value of the person at sea level.

6. The method of claim 1, further comprising, prior to the determining of the preferred dosage based at least in part upon the at least subset of the number of Sleep-Disordered Breathing (SDB) severity values, determining an initial preferred dosage based at least in part upon a data set that includes one or more SDB severity values and one or more corresponding effective altitude values and one or more corresponding dosages of the CSA treatment for a number of other individuals having altitude-induced CSA.

7. An apparatus structured to be worn on a body of a person and automatically and dynamically titrate treatment for altitude-induced Central Sleep Apnea (CSA) for the person, comprising:
   a processor apparatus comprising a processor and a storage;
   an input apparatus structured to provide a number of input signals to the processor apparatus;
   an output apparatus structured to receive a number of output signals from the processor apparatus; and
   the storage having stored therein a number of instructions which, when executed on the processor, cause the apparatus to perform a number of operations comprising:
   for each of a number of periods of sleep of the person, determining a number of Sleep-Disordered Breathing (SDB) severity values, each SDB severity value of the number of SDB severity values being based at least in part upon a corresponding effective altitude value and a corresponding dosage of a CSA treatment;
   automatically determining a current effective altitude of the person;
   determining based at least in part upon at least a subset of the number of Sleep-Disordered Breathing (SDB) severity values and the current effective altitude, a preferred dosage of the CSA treatment at which a likely SDB severity value is no greater than a predetermined SDB severity value; and
   generating an output from the apparatus indicating a recommended treatment for CSA at the preferred dosage of the CSA treatment.

8. The apparatus of claim 7 wherein the preferred dosage is a minimum dosage of the CSA treatment at which the likely SDB severity value is no greater than the predetermined SDB severity value.

9. The apparatus of claim 7 wherein the operations further comprise generating the output at a time approaching a habitual bedtime of the person.

10. The apparatus of claim 7 wherein the output is further representative of the person being at or above the given effective altitude.

11. The apparatus of claim 7 wherein each SDB severity value of at least some of the number of SDB severity values is further based at least in part upon an SDB severity value of the person at sea level.

12. The apparatus of claim 7 wherein the operations further comprise, prior to the determining of the preferred dosage based at least in part upon the at least subset of the number of Sleep-Disordered Breathing (SDB) severity values, determining an initial preferred dosage based at least in part upon a data set that includes one or more SDB severity values and one or more corresponding effective altitude values and one or more corresponding dosages of the CSA treatment for a number of other individuals having altitude-induced CSA.

* * * * *